(12) United States Patent
Vuorenkoski-Dalgleish et al.

(10) Patent No.: US 10,088,571 B2
(45) Date of Patent: Oct. 2, 2018

(54) UNDERWATER SENSING SYSTEM

(71) Applicant: FLORIDA ATLANTIC UNIVERSITY, Boca Raton, FL (US)

(72) Inventors: Anni Vuorenkoski-Dalgleish, Vero Beach, FL (US); Fraser Dalgleish, Vero Beach, FL (US); Bing Ouyang, Vero Beach, FL (US)

(73) Assignee: FLORIDA ATLANTIC UNIVERSITY BOARD OF TRUSTEES, Boca Raton, FL (US)

(*) Notice: Subject to any disclaimer, the term of this patent is extended or adjusted under 35 U.S.C. 154(b) by 437 days.

(21) Appl. No.: 15/045,980

(22) Filed: Feb. 17, 2016

(65) Prior Publication Data

US 2016/0238698 A1    Aug. 18, 2016

Related U.S. Application Data

(60) Provisional application No. 62/117,199, filed on Feb. 17, 2015.

(51) Int. Cl.
| | |
|---|---|
| *G01C 3/08* | (2006.01) |
| *G01S 17/88* | (2006.01) |
| *G01S 17/00* | (2006.01) |
| *G01S 17/10* | (2006.01) |
| *G01S 7/497* | (2006.01) |
| *G01N 21/53* | (2006.01) |

(52) U.S. Cl.
CPC .............. *G01S 17/88* (2013.01); *G01S 7/497* (2013.01); *G01S 17/003* (2013.01); *G01S 17/10* (2013.01); *G01N 21/538* (2013.01)

(58) Field of Classification Search
CPC ........ G01S 17/88; G01S 7/497; G01S 17/003; G01S 17/10; G01N 21/538
See application file for complete search history.

(56) References Cited

U.S. PATENT DOCUMENTS

| 7,961,301 B2* | 6/2011 | Earhart | G01S 3/7867 356/4.01 |
|---|---|---|---|
| 9,041,915 B2* | 5/2015 | Earhart | G01S 3/7867 356/220 |
| 2012/0050750 A1* | 3/2012 | Hays | G01J 9/04 356/519 |

(Continued)

*Primary Examiner* — Samantha K Abraham
(74) *Attorney, Agent, or Firm* — Fox Rothschild LLP

(57) ABSTRACT

Methods for characterizing scattering in a medium of a Light Detection And Ranging (LiDAR) system and systems therefrom are provided. A method includes obtaining off-axis power return characteristics with respect to a first wavelength of light and on-axis power return characteristics for at least the first wavelength of light. The method also includes estimating at least one beam attenuation coefficient (c) based on the off-axis power return characteristics and common volume parameter function for the LiDAR system and an extinction coefficient ($\alpha$) for the medium based on the on-axis power return characteristics. The method further includes extracting a value for at least one diffuse attenuation coefficient ($K_d$) for the medium using a beam spread parameter for the LiDAR system (D) and a pre-defined relationship between $\alpha$, c, D, and $K_d$.

20 Claims, 13 Drawing Sheets

(56) References Cited

U.S. PATENT DOCUMENTS

| | | | |
|---|---|---|---|
| 2012/0169053 A1* | 7/2012 | Tchoryk, Jr. ............. | G01P 5/26 290/44 |
| 2012/0274937 A1* | 11/2012 | Hays ....................... | G01S 17/58 356/337 |
| 2013/0314694 A1* | 11/2013 | Tchoryk, Jr. ............ | G01S 17/95 356/28.5 |

* cited by examiner

200

UNDERWATER SENSING SYSTEM

CROSS-REFERENCE TO RELATED APPLICATIONS

This application claims to priority to and the benefit of U.S. Provisional Patent Application No. 62/117,199, entitled "LiDAR SYSTEM AND INVERSION ALGORITHM FOR TURBID ENVIRONMENTS and filed Feb. 17, 2015, the contents of which are hereby incorporated by reference in their entirety.

STATEMENT REGARDING FEDERALLY FUNDED RESEARCH

This invention was made with government support under Award No. N00014101091 awarded by Office of Naval Research. The government has certain rights in the invention.

FIELD OF THE INVENTION

The present invention relates to underwater sensing systems, and more specifically to apparatus and methods for implementing water sensing systems in scattering environments.

BACKGROUND

In general, conventional methods to correct for the Multiple Scattering (MS) errors in the Light Detection And Ranging (LiDAR) inversion have been based on existing work on bi-static imaging LiDAR. This work has uncovered that deviation in photon transport path due to multiple scattering events have both spatial and temporal effects, which can be measured with a single channel receiver system. Based on this work, state-of-the-art LiDAR imaging systems are typically configured to utilize polarization-sensitive, range-gating and model-based techniques to remove the MS contribution of the signal to improve the contrast of the target signal.

Typically, the interpretation of LiDAR return signals is based on so-called Single Scattering (SS) assumption. This theory for the interpretation of LiDAR return signals provides a solution for attenuation and backscattering inversion. However the scattering and radiative transfer theory within the basic LiDAR equation assumes that each received photon has experienced only one scattering event and therefore the backscattering information can be assumed to have resulted from a single scattering particle. However, radiative transfer in scattering media is not limited to SS, or so-called Common Volume (CV), processes. Rather, photon transport may also involve Multiple Scattering (MS) processes, also called Non-Common Volume Scattering (NCV), as well as SS processes. These scattering processes are schematically illustrated in FIG. 1. Consequently, there has been some interest in studying the combination of MS and the CV contributions in LiDAR signals in order to develop correction methods for MS "noise", which would allow the retrieval of Inherent Optical Properties (IOPs) of the medium. These properties, particularly the attenuation coefficient and the scattering coefficient, are critical parameters used in many oceanographic applications, like underwater imaging, optical communications, underwater object detection and tracking, sensing and domain awareness, environmental monitoring and ecological health assessment.

Currently, the measurements of the IOPs are carried out with in-situ sensors, which typically utilize a very small measurement volume. Further, in order to resolve depth-dependent attenuation profiles combining depth (or range) resolved information on layers consisting of varying scattering and absorption properties, the instruments are deployed in a profiling platform and lowered through the water column. However, these methods are very slow, intrusive and ineffective when measuring dynamic events. Thus, there is a need to provide optical property information through inhomogeneous media without disturbing the measurement volume.

SUMMARY

Embodiments of the invention concern an underwater sensing system that includes a plurality of transmitters at selectable wavelengths, that rapidly scan an array of laser pulses into the water column, and a plurality of staring receivers that measure the two-dimensional arrays of backscatter profiles, with fine spatial and temporal resolution, with selectable spectral and polarization sensitivity. The system further includes an algorithm that inverts and corrects the recorded two-dimensional arrays of backscatter profiles into accurate beam attenuation coefficients and other water column properties at each wavelength.

In a first embodiment of the invention, there is provided a method for characterizing scattering in a medium of a Light Detection And Ranging (LiDAR) system. The method includes obtaining off-axis power return characteristics with respect to a first wavelength of light and on-axis power return characteristics for at least the first wavelength of light. The method further includes estimating at least one beam attenuation coefficient (c) based on the off-axis power return characteristics and common volume parameter function for the LiDAR system and an extinction coefficient ($\alpha$) for the medium based on the on-axis power return characteristics. The method additionally includes extracting a value for at least one diffuse attenuation coefficient ($K_d$) for the medium using a beam spread parameter for the LiDAR system (D) and a pre-defined relationship between $\alpha$, c, D, and $K_d$.

The method can further include adjusting imaging data for the LiDAR system based on the value for $K_d$. Also, the wavelengths of light used can be in the range between 400 nm and 750 nm.

In the method, the off-axis power return characteristics can include a total energy multiple scattering (MS) return, a total energy single scattering return, and a beam spread for the first wavelength of light. Further, estimating the beam attenuation coefficient can include computing a ratio of a total power during a Non-Common Volume Scattering (NCV) period and a total power during the a Common Volume Scattering (CV) period scaled by the common volume parameter for the first wavelength of light, wherein the total power during the NCV period is derived from the total energy MS return, and wherein the total power during the CV period is derived from the total energy SS return.

In the method, the on-axis power return characteristics can include an instantaneous power as a function of time, the peak instantaneous power, and the slope of decay of instantaneous power.

In the method, the obtaining can include obtaining the on-axis power return characteristics for at least one second wavelength of light and performing the estimating and extracting based on the on-axis power characteristics for the first wavelength of light and the at least one second wavelength of light.

In a second embodiment of the invention, there is provided a LiDAR system including a light source, an on-axis sensor an off-axis sensor, and a computing system coupled to at least the on-axis sensor and the off-axis sensor, the computing system comprising a processor and a memory having stored therein instructions for causing the process to perform the steps of method in the first embodiment.

In a third embodiment, there is provided a computer-readable medium having stored therein a computer program for causing a computing device to characterize scattering in a medium of a Light Detection And Ranging (LiDAR) system, the computer comprising a plurality of code sections for performing the steps of the method of the first embodiment.

DETAILED DESCRIPTION

Figure 1:
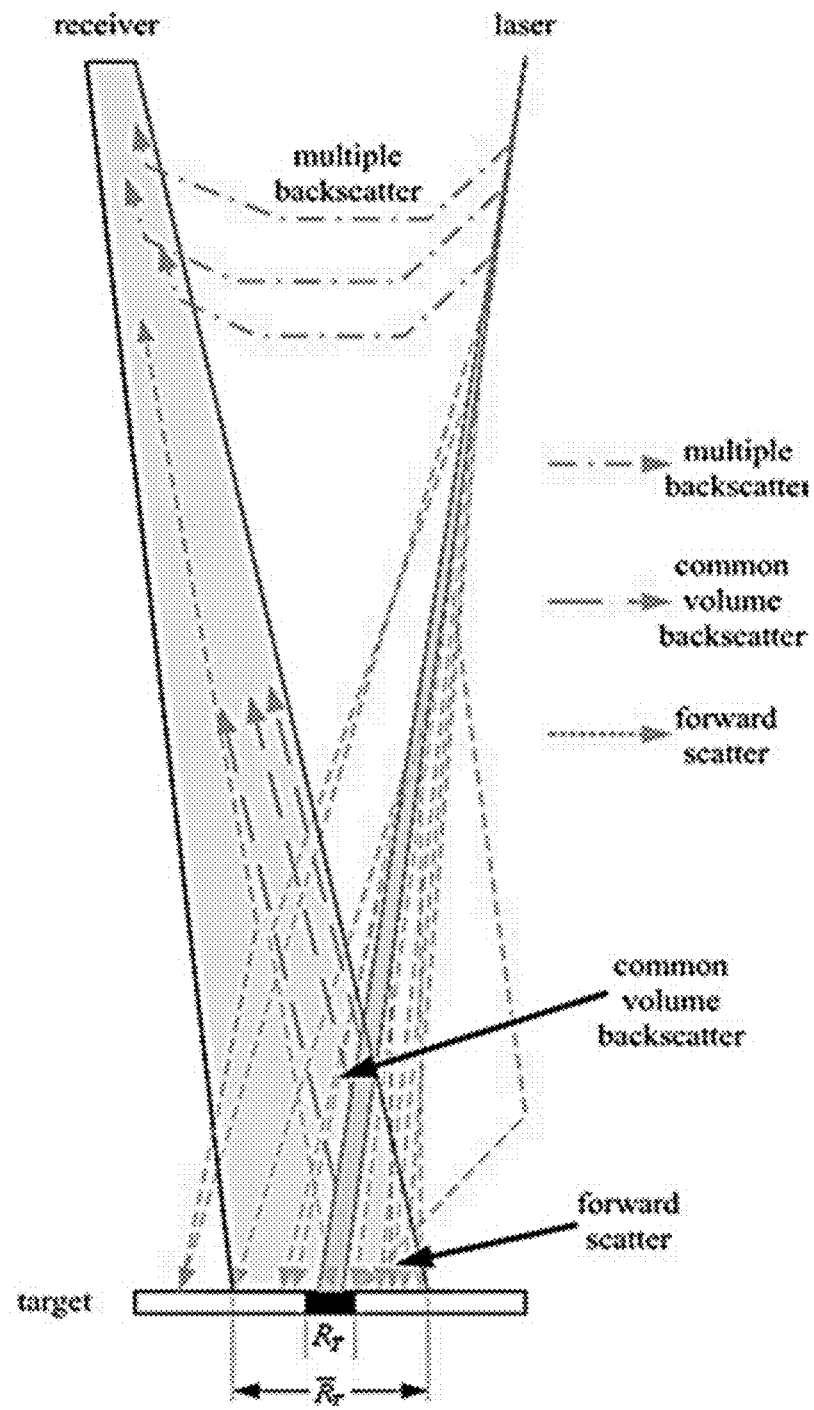
FIG. 1 shows a schematic of typical scattering processes in a bi-static LiDAR configuration.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments of the invention are directed to systems and methods for acquiring an instantaneous time-resolved optical backscattering return from a water column, which can be inverted to represent depth-resolved attenuation coefficient profile by employing a direct measurement of spatial and temporal dispersion to isolate the MS contribution.

An underwater Light Detection and Ranging (LiDAR) system in according to the present invention includes a transmitter assembly, which is comprised of a pulsed light source or multiple pulsed light sources of multiple wavelengths and a scanner, defining the pulse direction and the optical transmission path to provide illumination for the volume in the water column. The system also includes a receiver assembly for defining a return optical transmission path from the measurement volume and collecting the return signals from the volume. The transmitter assembly and the receiver assembly are separated so that there are distinct volumes associated with CV and NCV volumes. Further, the system includes a data storage and a processing component configured for implementing a methods according to the invention for estimating beam and diffusion coefficients in the sensor near-field and attenuation profiles in the far field.

The methods according to the invention for estimating beam and diffusion coefficients in the sensor near-field and attenuation profiles in the far field involve directing pulses in a water column and collecting time-resolved back-scattered light intensity. A receiver time-history consisting of multiple data points or bins can then be directly related to temporal and spatial characteristics of the measurement volume. The signal can then be related to scattering events originated in either CV or NCV, and also can also be related to range through a priori knowledge of the speed of light in the transmission and scattering medium. The methods can also involve a signal processing algorithm to compute the relative signal energy returned from CV and NCV, which is then used to estimate the beam temporal and spatial dispersion characteristics resulting from single or multiple scattering events. These characteristics can then be used to estimate the beam and diffusion attenuation coefficients in the sensor near-field and attenuation profiles in the far field.

In some embodiments, a serially scanned laser beam transmitter can be utilized and can also be used to measure the structure of the volume scattering function in both the backward and the forward directions. This information can then also directly be used to estimate the point spread function for an imaging system, and as such can be used to correct for the effects of scattering, through-the-sensor.

These systems and methods will be described below in greater detail.

The design of the LiDAR system and methods according to the present invention design are driven by a significant fundamental criterion—the ability to conduct the primary processing on-board. The process to invert the acquired waveform, or LiDAR return, is better established for atmospheric LiDAR systems, where optical densities are significantly lower, and gradients larger than in marine environment. The basic single scattering LiDAR equation:

$$P(r) = C\frac{\beta_\pi(r)}{r^2}e^{-2\int_0^r \alpha(r')dr'} \quad (1)$$

where C is a LiDAR system constant that combines effects due to optical configuration and sensitivity, $\beta_\pi[m^{-1}\,sr^{-1}]$ is the total angular volume scattering coefficient at 180° scattering angle, r [m] is the range and $\alpha[m^{-1}]$ is the total attenuation coefficient, involves assumptions that have a significant impact on the derivation of attenuation coefficient from the raw signal. While the equation is ill-posed, ample past and present studies have been conducted to develop methods to transform the instantaneous power of the analog photodetector output to range-resolved extinction coefficient in atmospheric systems and oceanic systems.

The main challenge of the LiDAR equation is the exclusion of the effects of multiple scattering (MS), which results in an increase in light return and a subsequent decrease in the effective extinction coefficient estimation. The magnitude of this effect is determined by the photon mean free path in the medium, the volume scattering function of the suspended particles, and the system architecture, mainly the receiver field of view, the acceptance function, and the source beam divergence. A large number of studies have been carried out to quantify this effect, including Monte Carlo methods, Small-Angle Approximation (SAA) methods, and methods relating multiple scattering to depolarization. However, a practical implementation of these methods have been limited due to the operational requirements for on-board autonomous LiDAR. That is, a model-based estimation of higher-order scattering contribution requires significant on-board processing capacity and also requires a priori knowledge of the medium properties, such as the Volume Scattering Function (VSF) and the single scattering albedo. The polarization based methods, despite of enhancing the contrast of thin layers, complicate the receiver optics, reduce signal-to-noise ratio, and introduce ambiguity due to other mechanisms transforming the Stokes vector (VSF and particle morphology).

The MS correction according to the present invention is based on the simultaneous coaxial and biaxial returns. The off-axis return provides a direct measurement of the spatial spreading of the beam due to the MS in the range between the instrument and the CV, and is also inverted in the estimate of range-averaged beam attenuation in the same range. The parameters obtained provide an estimate to invert the effective (measured) extinction coefficient ($\alpha_e$) to theoretical extinction coefficient ($\alpha$), beam attenuation coefficient (c), and diffuse attenuation coefficient ($K_d$). The influence of MS to $\alpha$, c and $K_d$ has been previously modeled using Monte Carlo methods and has recently been presented as a function of beam attenuation coefficient c and beam divergence (D). Such modeling has been used to derive various types of relationships between $\alpha$, c, D, and $K_d$. Such relationships are used in the various embodiments of the invention to support an empirical MS correction methodology. In particular, the present invention provides a method to use the CV/NCV return to directly measure a parameters c and D in such relationships.

For ease of explanation, the empirical correction methodology according to the present invention will be described using the following relationship:

$$\alpha = K_d + (c - K_d) e^{-85 c D}, \quad (2)$$

which requires system-specific calibration but no a priori knowledge of VSF is required to estimate the c and the MS contribution and a/c. The relationship in equation (2) was described in Churnside, J. H., 2014, Review of profiling oceanographic lidar. Opt. Eng. 53, 051405, the contents of which are hereby incorporated by reference in their entirety. The relationship of equation (2) is important and useful in the various embodiments because it relates spatial divergence to attenuation coefficients. However, the present invention can be implemented using other relationships between $\alpha$, c, D, and $K_d$.

The methodology according to the present invention is described in detail below with respect to FIGS. 1, 2A, 2B, and 2C. Throughout these figures and the discussion below, reference will be made to the following terms:

FOV—Field of view
MS—Multiple scattering
SS—Single Scattering
P—Power

In particular, the above-mentioned figures describe the quasi-single scattering inversion algorithm and the primary processing of the pulse return. The MS correction according to the present invention relies on (1) the direct measurement of beam spread and (2) the direct knowledge of the effects of geometrical system-specific parameters (source-receiver separation, receiver field-of-view, source scan/pointing angle, etc.). While (2) is easily quantifiable via experiment means, (1) is a more complex measure, due to a number of unknown factors, which have a role in determining the photon transport characteristics, and hence the ultimately the measured beam spread. Thus, this invention provides a non-modeling based solution to compensate for how beam and diffuse attenuation coefficients and related beam spread affects the slope of the LiDAR return.

Figure 2:
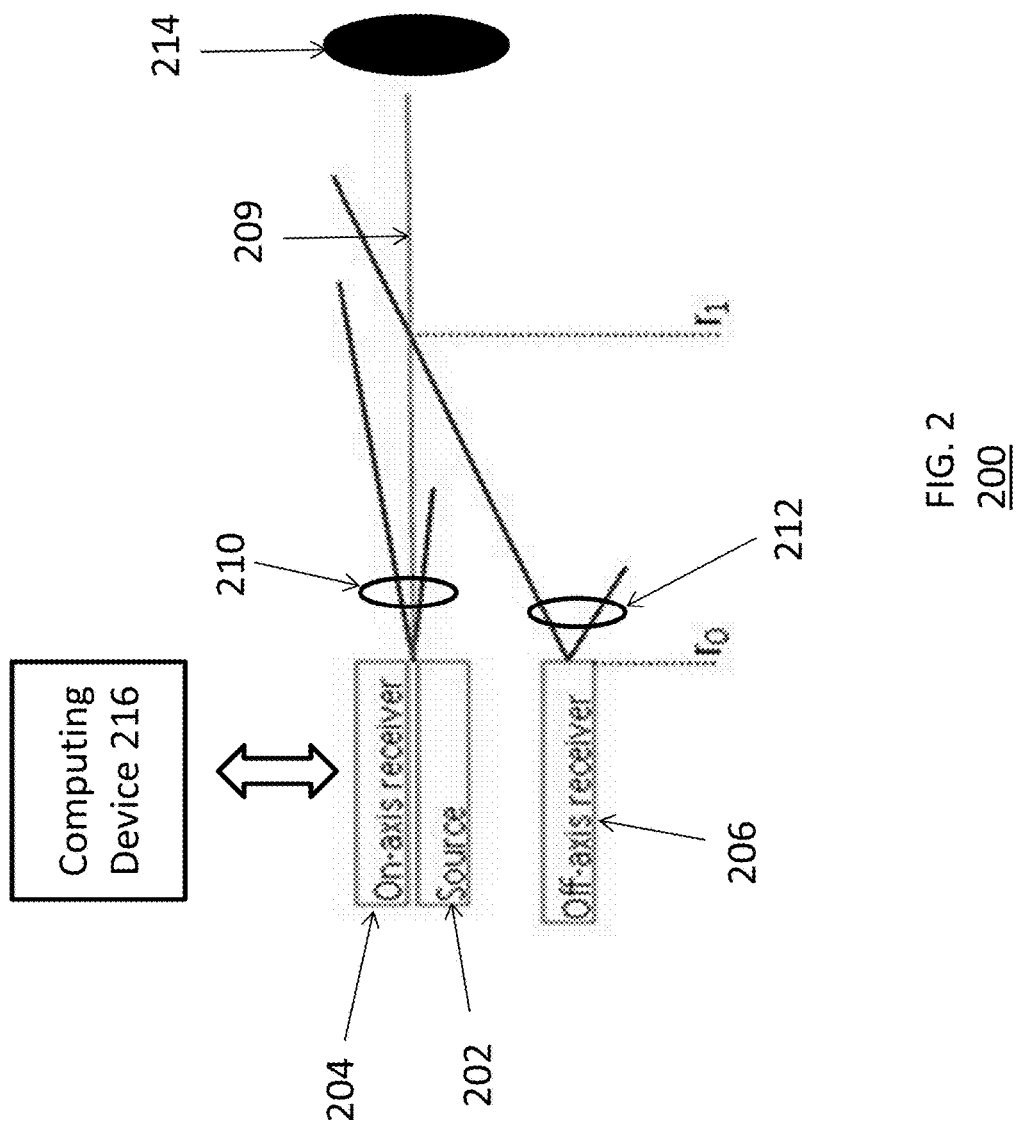
FIG. 2 shows a schematic view of a system according to the present invention.

Turning first to FIG. 2, there is shown a basic schematic of a LiDAR system 200. The system 200 includes a light source 202, an on-axis receiver 204 and an off-axis receiver 206. The light source 202 provides one or more light (laser) beams 208 at different wavelengths. The on-axis receiver 204 is configured to detect one or more wavelengths of light falling within a first field of view 210. The off-axis receiver 206 is configured to detect one or more wavelengths of light falling within a second field of view 212. In operation, the light beam 208 is shone on a target area 214. Any light reflected from the target area 214 can then be detected by either of receivers 204 and 206 as long as the direction of travel is along a corresponding field of view 210 and 212. The components of system 200 can be controlled and monitored using a computing device 216, which can be configured to perform the various processes described below.

Additional details of imaging systems capable of implementing and using the methodologies discussed herein are provided in U.S. Pat. No. 8,917,395 to Dalgleish et al., issued Dec. 23, 2014, and U.S. Pat. No. 9,019,503 to Ouyang et al., issued Apr. 28, 2015, the contents of both of which are hereby incorporated by reference in their entirety.

Figure 3A:
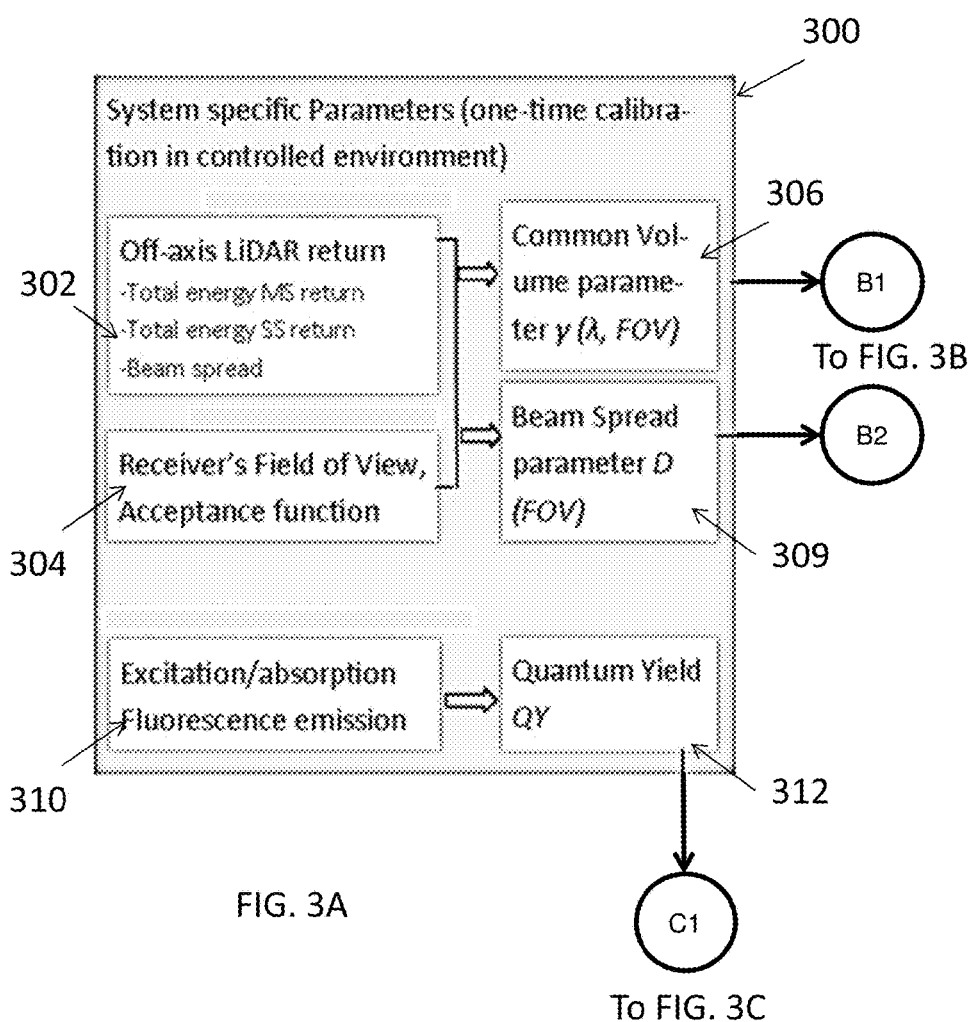
FIGS. 3A, 3B, and 3C show a methodology according to the present invention.
Figure 3B:
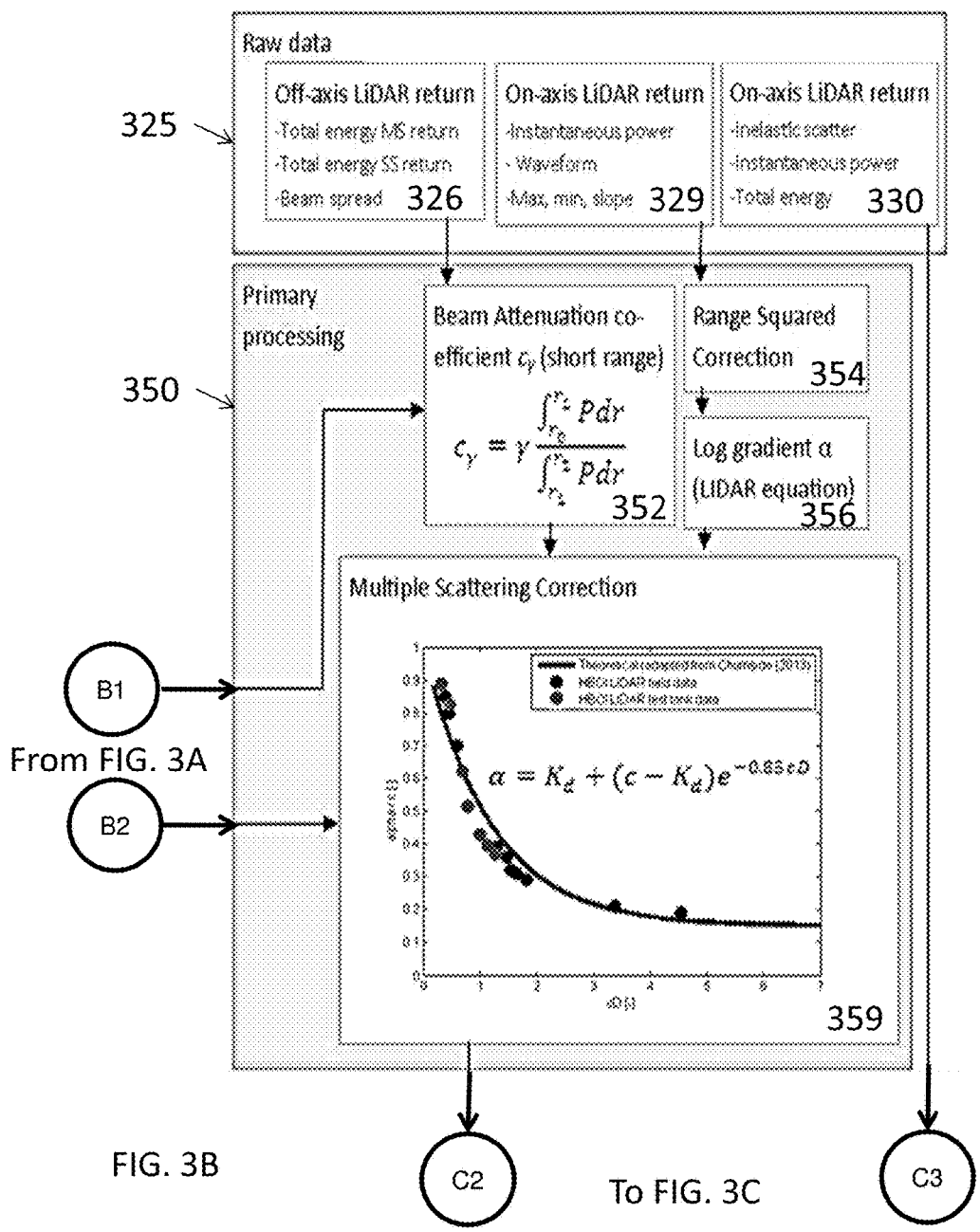
Figure 3C:
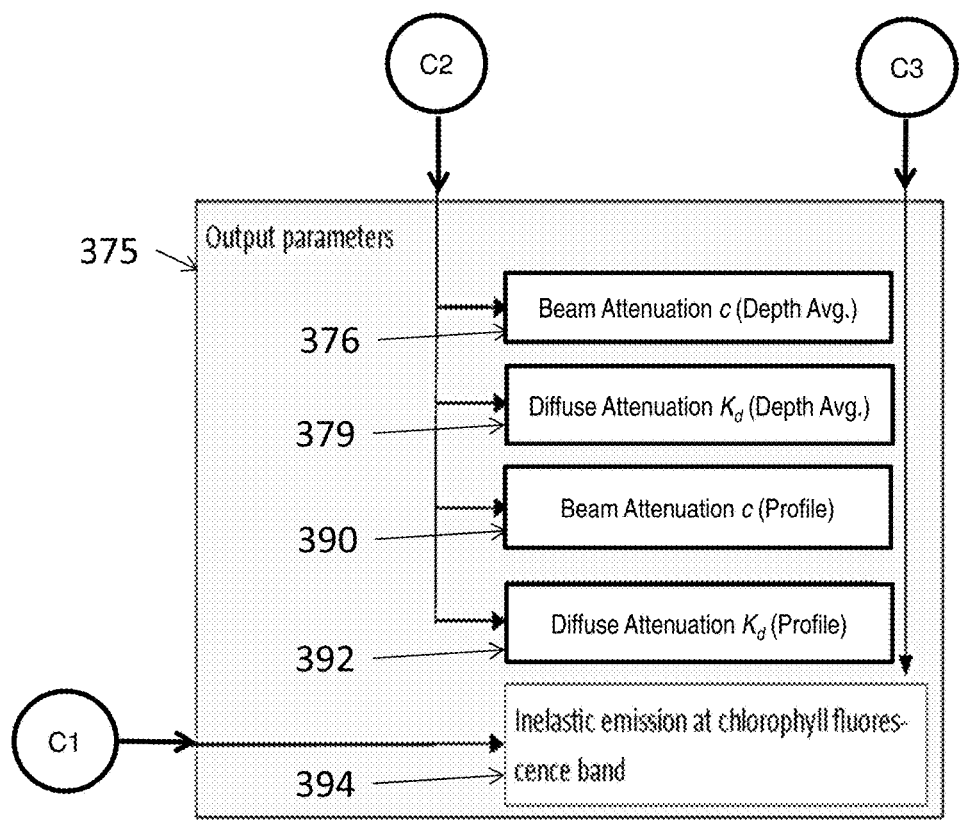

Details of the methodology are described in FIGS. 3A, 3B, and 3C. Turning first to FIG. 3A, there is shown a calibration process 300 for the methodology according to the present invention. This calibration process 300 is generally conducted one time to calibrate the LiDAR system. However, the present invention is not limited in this regard and the calibration process 300 can be performed as many times as necessary.

Figure 4:
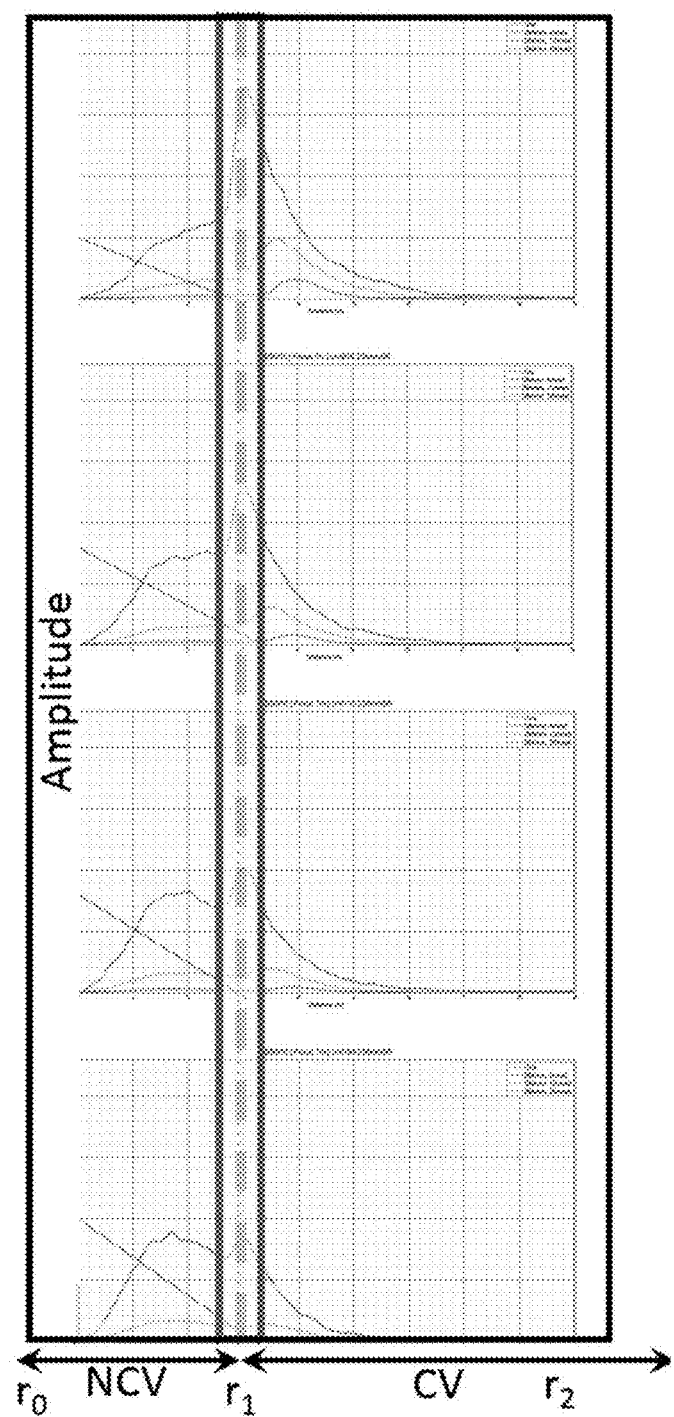
FIG. 4 shows experimental illustrating CV and NCV periods.

The calibration process 300 involves performing measurements in a controlled environment in order to extract system-specific parameters. In particular, a common value parameter γ (A, FOV) and a beam spread parameter D (FOV). The first two parameters, the common value parameter γ (A, FOV) and the beam spread parameter D (FOV) are obtained based on a first set of measurements at 302 and 304. This process is described in greater detail below with respect to FIG. 4. FIG. 4 illustrates various plots exemplary LiDAR waveform amplitude as a function of time.

As illustrated in FIG. 4, a measured LiDAR waveform is divided in two sections in the temporal domain. First, there is the NCV time period, during which the light pulse, or the photon packet, travels from the transmitter exit orifice ($r_0$) to the point where the pulse enters the receiver's field of view ($r_1$). Second, there is the CV period, which is the time period from $r_1$ to the point where the pulse is completely attenuated ($r_2$). The output of the receiver is in volts, which is assumed to have a linear and well characterized relationship to the received optical power. The energies, referred at 302, are then the integrals of this power over time periods NCV and CV. Thereafter, the ratio of the return energy during the NCV period to the energy during CV period responds linearly to the beam attenuation coefficient c:

$$c_\gamma = \gamma \frac{\int_{r_0}^{r_1} P\,dr}{\int_{r_1}^{r_2} P\,dr}, \quad (3)$$

where P is the measured total energy return. The calibration can be completed in a controlled environment using a standard turbidity cycle, since in such environments c can be independently controlled and verified. This measurements can then be used to obtain the common volume parameter γ (A, FOV), which will account for system-specific factors affecting the relationship between c and the ratio of common volume energies.

Thus, at 302, measurements at different wavelengths are taken via the off-axis receiver. From these measurements, one can measure a total energy MS (energy during the NCV period) return, a total energy SS (energy during the CV period) return, and the beam spread at 302. In one configuration, the wavelengths can be between 400 and 750 nm. The precise wavelengths to be used can depend on a variety of factors, including, but not limited to the characteristics of the medium of interest and/or the types of particles in the medium. However, the present invention is not limited to any particular wavelengths.

At 304, the system specific parameters are measured and verified, which are functions of the system geometry, i.e. the receiver's field of view, the receiver's acceptance function and the source-receiver separation. These system-specific parameters, together with the beam spread at 302, collectively translate to a single parameter D(FOV) at 308.

Optionally and before, after, or contemporaneously with the measurements at 302 and 304, the system can also perform measurements at 310 of excitation/absorption and fluorescence emission. In one configuration, the excitation/absorption measurements and the fluorescence emission measurements can be performed using wavelengths at or close to the two ends of the 400 nm to 750 nm range discussed above. However, the present invention is not limited to any particular wavelengths for these measurements. Thereafter, based on the measurements at 310, the quantum yield QY can be obtained at 312.

It should be noted that the measurements and parameter determinations in 300 can be performed using any number of wavelengths. However, the number of wavelengths to be used can vary depending on a variety of factors, including, but not limited to the characteristics of the medium of interest and/or the types of particles in the medium Once the system specific parameters are obtained, actual measurements can be performed and primary processing can be performed. This is illustrated with respect to FIG. 3B. FIG. 3B shows the processes for obtaining measurements, i.e., raw data, at 325, followed by processed for performing primary processing of the raw data at 350.

Turning first to the processes at 325 in FIG. 3B, two processes are performed to obtain the raw data. First, at 326, off-axis LiDAR return measurements are made to obtain the total energy MS return, the total energy SS return, and the beam spread. These measurements are performed in substantially the same way as at 302.

Second, at 328 on-axis LiDAR return measurements are made to obtain a waveform of the instantaneous power and to determine peak power and a slope of the decay.

Optionally, at 330, other on-axis LiDAR measurements can be made to obtain measurements of inelastic scatter, instantaneous power, and a total energy at least at the emission wavelengths used at 310.

After the raw data is obtained at 325, the raw data can undergo primary processing at 350. First, at 352, a short range beam attenuation coefficient $c_\gamma$ can be obtained based on the measurements at 326. As shown in FIG. 3B, this can be obtained by solving equation (3) in a manner similar to how γ was obtained at 306.

Before, after, or contemporaneously with the processing at 352, the processing at 354 and 356 can be performed based on the measurements at 328. First, a standard range square correction, which accounts for the quadratic decrease of the signal intensity with distance, is obtained at 354. Thereafter, the log gradient value a for the LiDAR equation, equation (1), is obtained at 356.

Once c and α are obtained at 352 and 356 and using the calibrated value for D from 308, field data for α/c and cD can be used to estimate the relationship between c and α at 358 and obtain Kd based on a pre-defined relationship. For example, the relationship in equation (2) and shown in FIG. 3B. However, as previously noted, other relationships can be used in the various embodiments of the present invention.

This is a critical step when relating the long range LiDAR attenuation profile to the attenuation coefficient. The LiDAR attenuation coefficient α, which essentially is the slope of the measured exponential return signal decay, responds to both beam attenuation coefficient c, which is a property very closely related to beam transmission through the Beer-Lambert law, and the diffuse attenuation coefficient, $K_d$. This relationship is fundamentally complex and is a function of several factors relating to LiDAR configuration, particularly the FOV, the transmitter wavelength, and the properties of the particles in the measurement volume (the volume scattering function and the single scattering albedo). For most applications, the more useful relation is the beam attenuation coefficient, which is an inherent optical property, and the relationship in this equation allows the relationship between the measured LiDAR attenuation and the long-range c to be established. The value for $K_d$ can thus be estimated from a direct measurement (assuming the FOV is wide enough to assume all forward scattered light remain in the measurement volume and hence the LiDAR return responds only to total absorption coefficient and the backscattering coefficient). Similarly, the current state of art estimates that c can be directly measured by using an infinitely small field of view (assuming the return responds to the entire volume scattering function and the total absorption. However, both of these measurements are based on the Single Scattering (SS) assumption and the theoretical basis will no longer be valid if the received photons have scattered more than once. Therefore, the present invention can now account for effects due to MS, which essentially is the factor cD, without making assumptions regarding the phase function and the albedo. In particular, by measuring the off-axis return, one can directly quantify the effect of the MS. As shown in FIG. 3B, the method has been validated by fitting experimental field and test tank data to the theoretical function, which has been selected for the known albedo (0.9) and phase function.

After the processes in FIG. 3B are completed, the methodology can proceed to FIG. 3C to output the final correction parameters. First, based on the information gleaned at 358, various output parameters can be output at 376, 378, 380, and 382. In particular, the depth averaged beam attenuation c can be output at 376 and the depth averaged diffuse attenuation $K_d$ can be output at 378. These depth averaged values output one attenuation value per waveform. Additionally, the profile beam attenuation c can be output at 380 and the profile diffuse attenuation $K_d$ can be output at 378. The profile values output one attenuation value at each range bin within the waveform.

Optionally, at 384, using the quantum yield QY obtained at 312 and the results at 330, the inelastic emission for a band of interest, such as a chlorophyll florescence band, can be obtained.

The parameters from FIG. 3C can then be used in a variety of ways. In some cases, the values can be used to adjust the attenuation parameters being used for LiDAR imaging. In particular, the improved parameters provided herein more accurately reflect the medium of interest and can therefore be used to improve the quality of the resulting image by accounting more accurately for the properties of the medium. Another application is to evaluate the medium over time, where the changes in the parameters can be used to track changes in the medium over time. In still another application, differences between different mediums can be more accurately determined.

Examples

The examples shown here are not intended to limit the various embodiments. Rather they are presented solely for illustrative purposes.

To demonstrate the effectiveness of the methodology of FIGS. 3A-3C, several experiments and simulations were performed. First, turning to FIG. 5 there is shown a schematic illustrating the experimental setup as well as the simulation environment being used.

Figure 5:
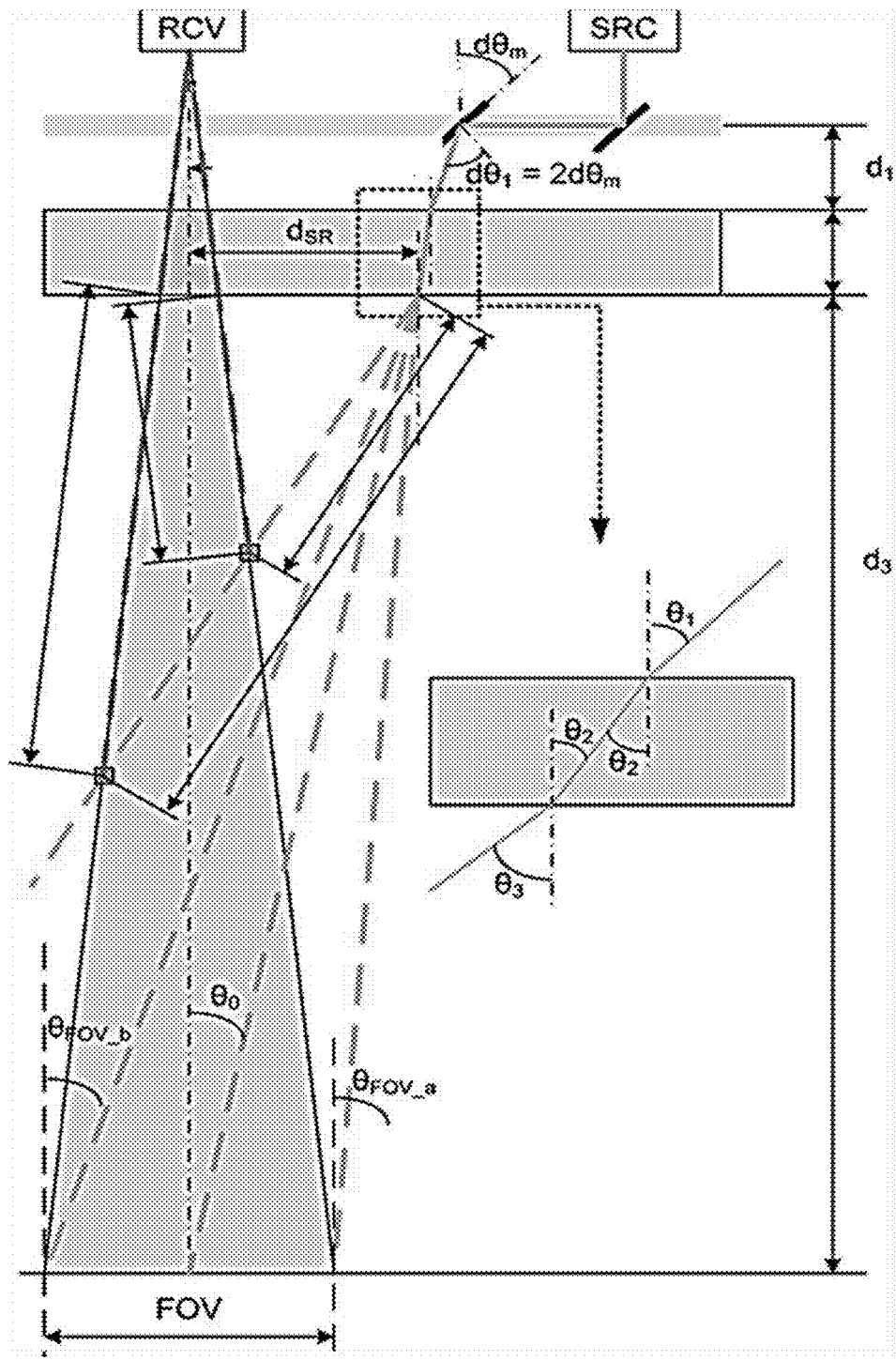
FIG. 5 shows a schematic illustrating and experimental set up for testing a methodology according to the present invention.

FIG. 5 shows the optical geometry for the multiple angle LiDAR, in this case how a fixed field of view (FOV) detector function (shaded triangle) overlaps with the scanning narrow collimated laser beam as a function of scan angle for a fixed separation distance ($d_{sr}$)

Figure 6:
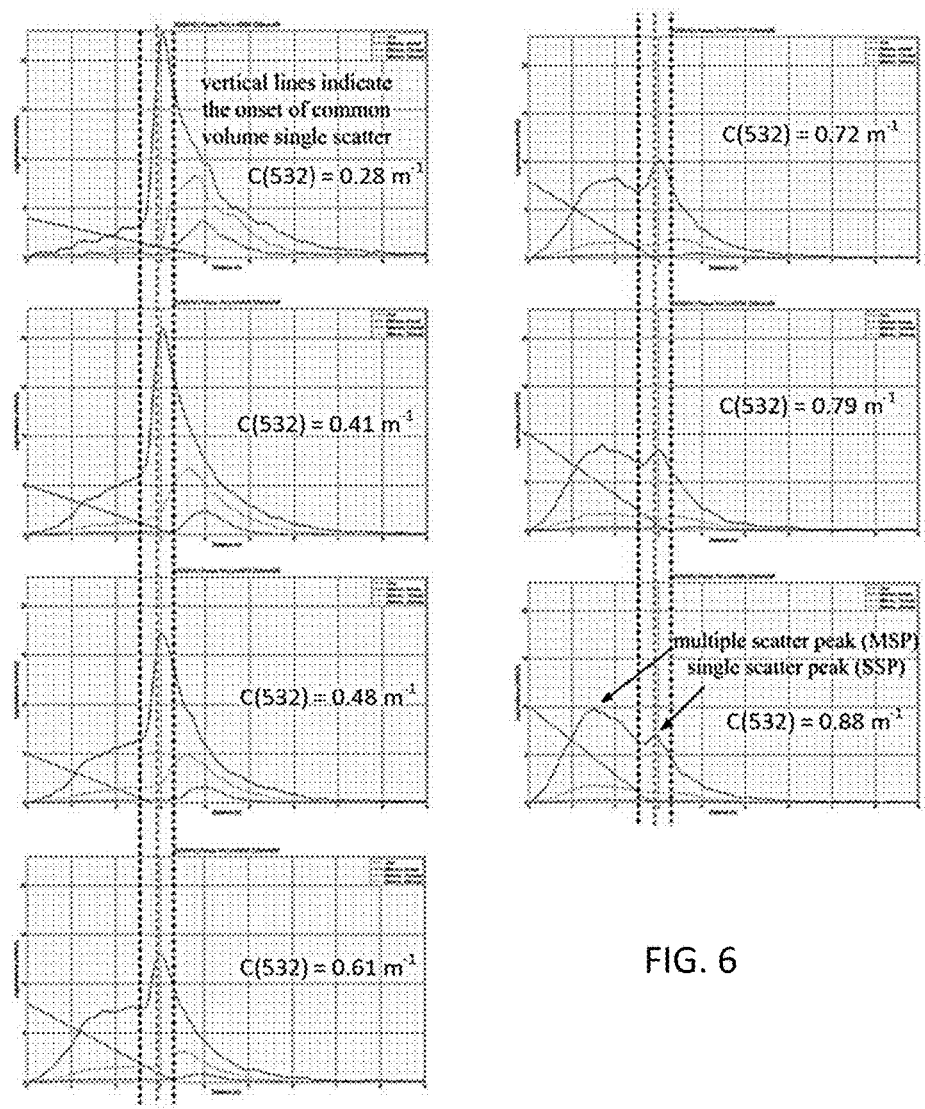
FIG. 6 shows experimental results showing the effect of the increasing turbidity on a receiver response.

FIG. 6 are experimental results showing the effect of the increasing turbidity on the receiver response. In particular, FIG. 6 shows plots of power as a function of time at three field of view (FOV) settings, taken through a turbidity cycle from clear water (c(532 nm)=0.28 $m^{-1}$) to turbid water (c(532 nm)=0.88 $m^{-1}$). The graphs in FIG. 6 clearly illustrate the proportionally between c and the ratio of MS/CV optical energies.

Figure 7A:
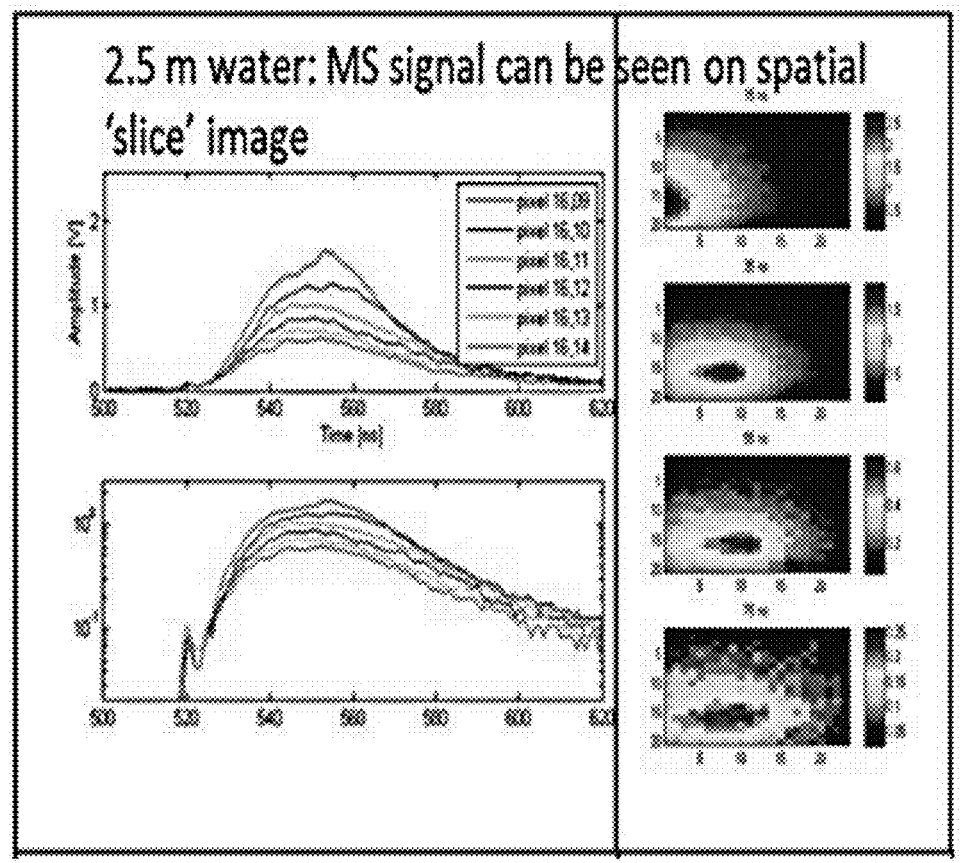
FIGS. 7A, 7B, and 7C shows experimental results from field testing in the Ligurian Sea using 2D scanning architecture, showing LiDAR-derived c-values before MS correction.
Figure 7B:
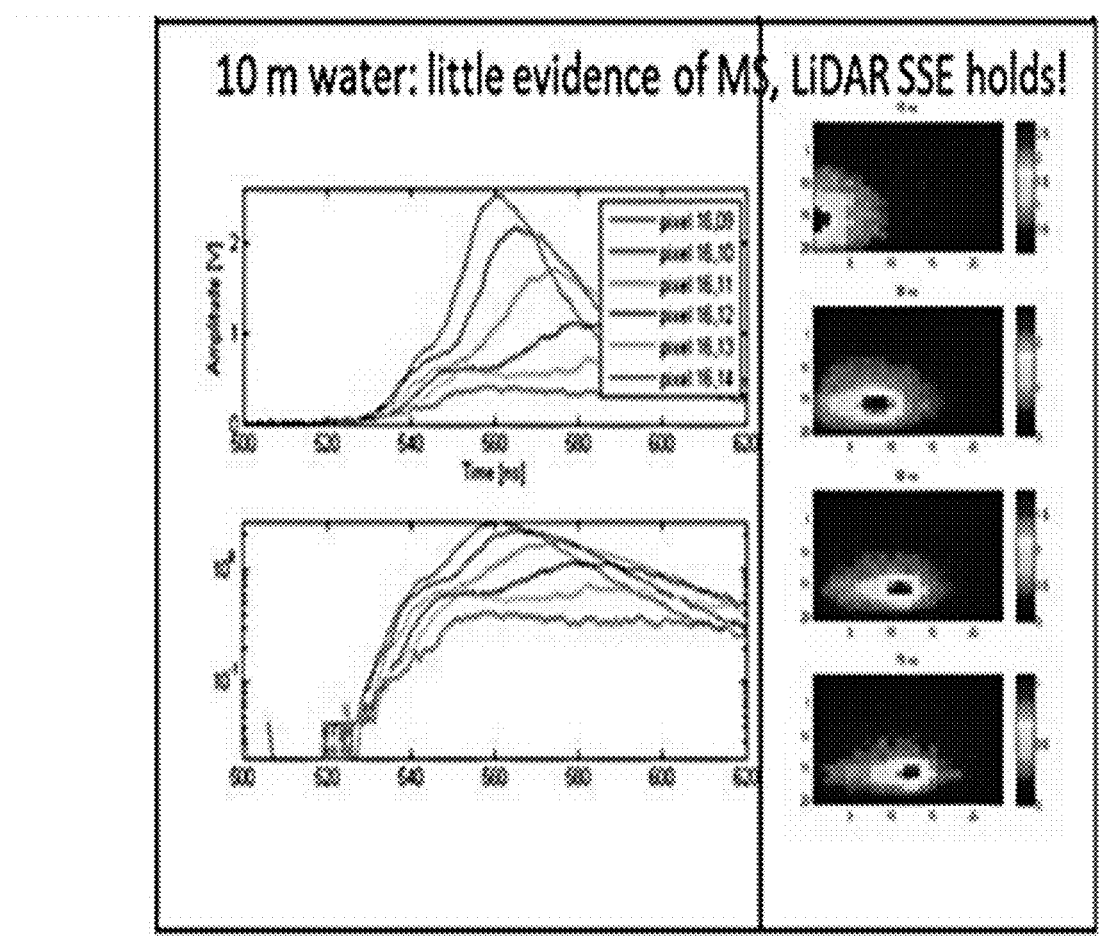
Figure 7C:
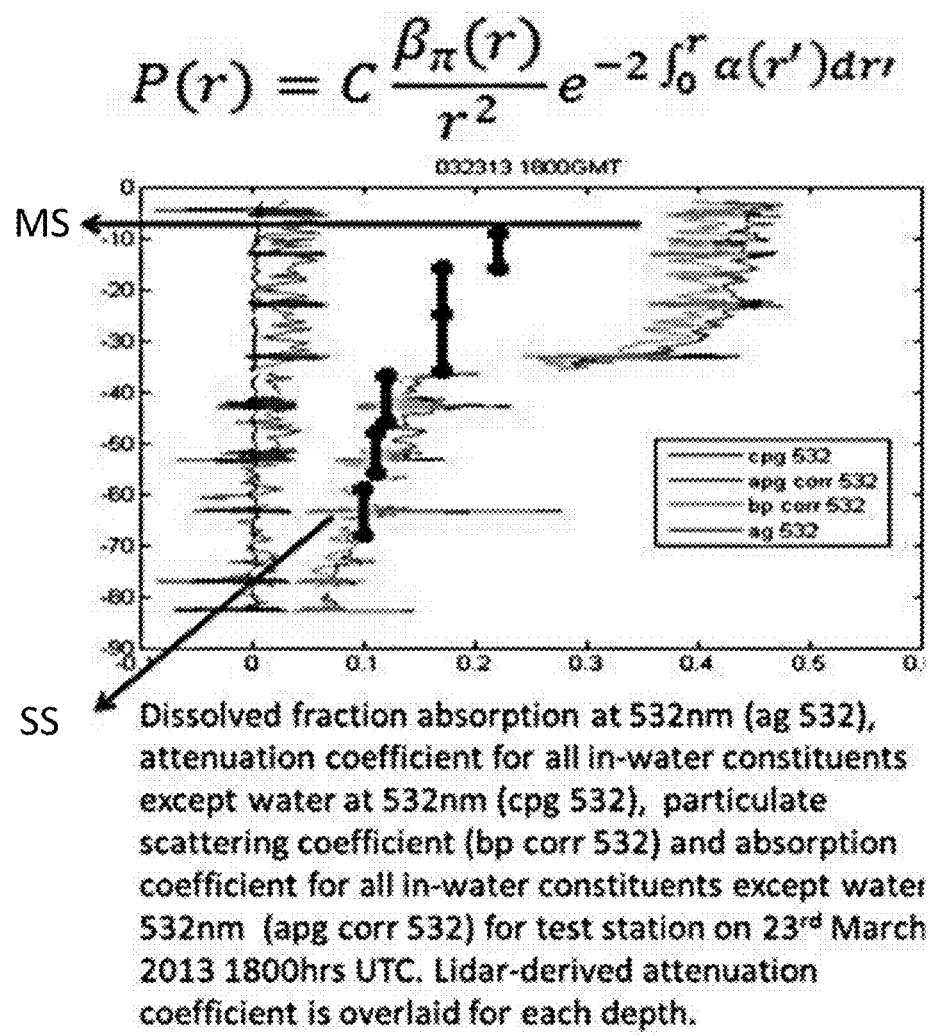

FIGS. 7A, 7B, and 7C shows experimental results from field testing in the Ligurian Sea using a 2D scanning architecture, showing LiDAR-derived c-values before MS correction. The results in FIGS. 7A-7C were obtained using a scanning mode to obtain the waveform of each pixel in the grid. This allows the forward and backward VSF to be derived.

In particular, FIG. 7A shows LiDAR images (right) for a depth visibility of 2.5 m, linear-linear (top left) and log-linear (bottom left) plots of voltage amplitude as a function of time. This set of images and waveforms were taken during an algae blooming event (beam c=1.2 m-1), representing 4 temporal or depth bins). FIG. 7A clearly shows that for the shallow visibility depth of 2.5 m, the MS contribution is clearly visible.

FIG. 7B shows LiDAR images (right) for a visibility depth of 10 m, linear-linear (top left) and log-linear (bottom left) plots of voltage amplitude as a function of time. This set of images and waveforms were taken in a clear water environment (c=0.08 m-1). The raster scan images clearly confirm both the spatial dispersion effects (beam spread), the associated near-field MS, and the range effects (α). FIG. 7B clearly shows that for the depth of 10 m, the MS contribution is less important and the SS contribution is more important.

FIG. 7C shows a plot of the LiDAR-retrieved depth averaged (one value per waveform) beam attenuation coefficient versus the all in-water constituents attenuation coefficients, dissolved fraction absorption coefficient, particulate attenuation scattering coefficient. These results are obtained using the single scattering (SS) LiDAR equation assumption and do not remove the underestimation of attenuation coefficient caused by MS. This figure shows a depth profile measured through the LiDAR, using the standard LiDAR equation to retrieve the long-range depth-averaged attenuation profile. The figure shows that without the MS correction routine, the c-value is significantly underestimated in higher turbidity environment. Also plotted in the figure is the profile measured concurrently with standard state of the art instrumentation.

Figure 8:
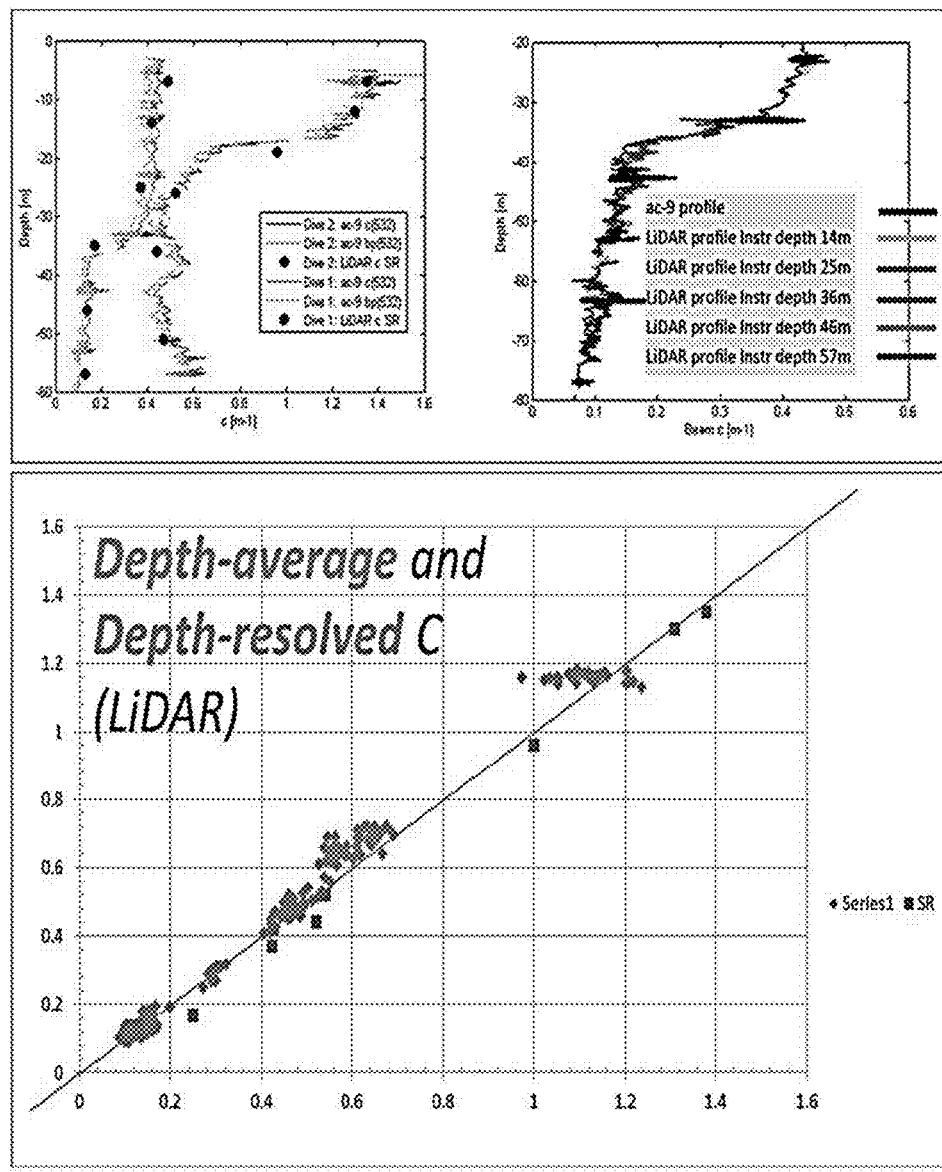
FIG. 8 shows experimental results from field testing in the Ligurian Sea using 2D scanning architecture, showing LiDAR-derived c-values after the MS correction.

FIG. 8 (top) shows experimental results from field testing in the Ligurian Sea using a 2D scanning architecture, showing LiDAR-derived c-values after the MS correction. In particular, FIG. 8 shows both depth-averaged on the top left (i.e. based on the $c_y$-parameter) and depth-resolved on the top right (based on the non-linear relationship between α, c, $K_d$ and D), after a correction has been applied. Both measures display excellent correlation with simultaneously measured α/c data. The bottom graph is a scatter plot between the LiDAR derived c and c independently measured by a state of the art instrument (WET Labs AC-9).

More specifically, FIG. 8 shows results from the same field deployment as FIGS. 7A-7C, but now corrected for the MS. The figure on the top left shows the short range c, while the figure on the top right shows the depth-resolved long range profile. Both figures also include the standard state-of-the-art instrument profiles for validation purposes. The bottom figure shows the same results, but now plotted against the standard state-of-the-art instrument data on the x-axis, demonstrating the point-by-point linearity.

Figure 9A:
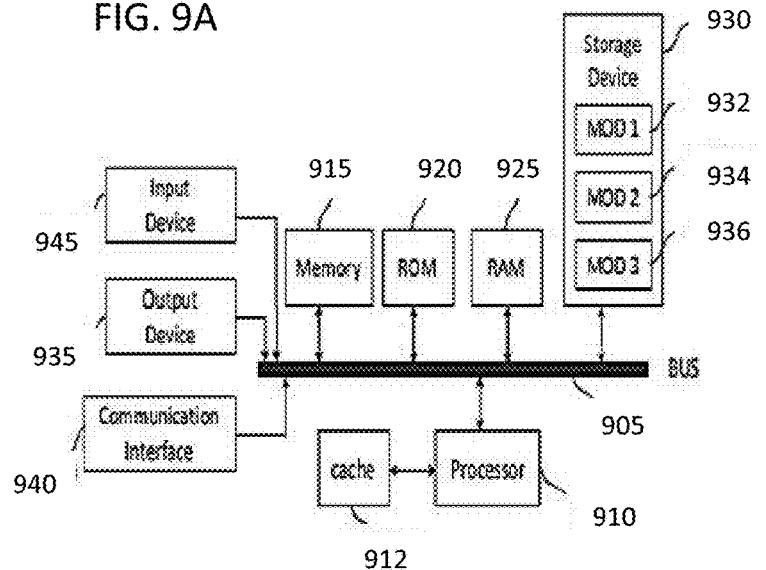
FIGS. 9A and 9B show a system configured for carrying one or more of the methods described herein.
Figure 9B:
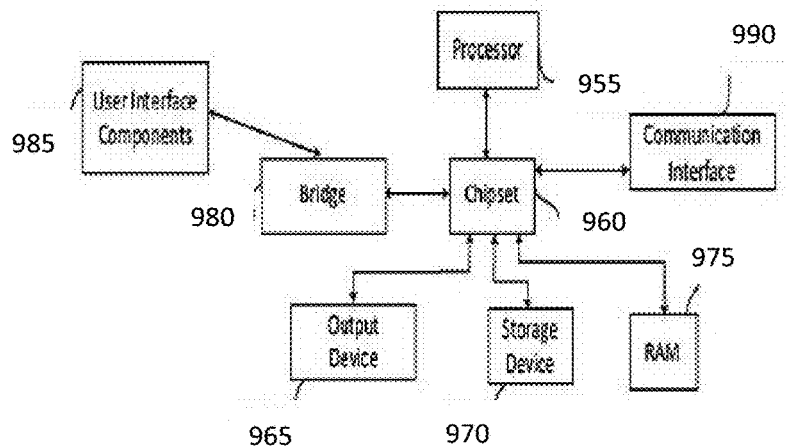

FIG. 9A, and FIG. 9B illustrate exemplary possible system configurations. The more appropriate configuration will be apparent to those of ordinary skill in the art when practicing the present technology. Persons of ordinary skill in the art will also readily appreciate that other system configurations are possible.

FIG. 9A illustrates a conventional system bus computing system architecture 900 wherein the components of the system are in electrical communication with each other using a bus 905. Exemplary system 900 includes a processing unit (CPU or processor) 910 and a system bus 905 that couples various system components including the system memory 915, such as read only memory (ROM) 920 and random access memory (RAM) 925, to the processor 910. The system 900 can include a cache of high-speed memory connected directly with, in close proximity to, or integrated as part of the processor 910. The system 900 can copy data from the memory 915 and/or the storage device 930 to the cache 912 for quick access by the processor 910. In this way, the cache can provide a performance boost that avoids processor 910 delays while waiting for data. These and other modules can control or be configured to control the processor 910 to perform various actions. Other system memory 915 may be available for use as well. The memory 915 can include multiple different types of memory with different performance characteristics. The processor 910 can include any general purpose processor and a hardware module or software module, such as module 1 932, module 2 934, and module 3 936 stored in storage device 930, configured to control the processor 910 as well as a special-purpose processor where software instructions are incorporated into the actual processor design. The processor 910 may essentially be a completely self-contained computing system, containing multiple cores or processors, a bus, memory controller, cache, etc. A multi-core processor may be symmetric or asymmetric.

To enable user interaction with the computing device 900, an input device 945 can represent any number of input mechanisms, such as a microphone for speech, a touch-sensitive screen for gesture or graphical input, keyboard, mouse, motion input, speech and so forth. An output device 935 can also be one or more of a number of output mechanisms known to those of skill in the art. In some instances, multimodal systems can enable a user to provide multiple types of input to communicate with the computing device 900. The communications interface 940 can generally govern and manage the user input and system output. There is no restriction on operating on any particular hardware arrangement and therefore the basic features here may easily be substituted for improved hardware or firmware arrangements as they are developed.

Storage device 930 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 925, read only memory (ROM) 920, and hybrids thereof.

The storage device 930 can include software modules 932, 934, 936 for controlling the processor 910. Other hardware or software modules are contemplated. The storage device 930 can be connected to the system bus 905. In one aspect, a hardware module that performs a particular function can include the software component stored in a computer-readable medium in connection with the necessary hardware components, such as the processor 910, bus 905, display 935, and so forth, to carry out the function.

FIG. 9B illustrates a computer system 950 having a chipset architecture that can be used in executing the described method and generating and displaying a graphical user interface (GUI). Computer system 950 is an example of computer hardware, software, and firmware that can be used to implement the disclosed technology. System 950 can include a processor 955, representative of any number of physically and/or logically distinct resources capable of executing software, firmware, and hardware configured to perform identified computations. Processor 955 can communicate with a chipset 960 that can control input to and output from processor 955. In this example, chipset 960 outputs information to output 965, such as a display, and can read and write information to storage device 970, which can include magnetic media, and solid state media, for example. Chipset 960 can also read data from and write data to RAM 975. A bridge 980 for interfacing with a variety of user interface components 985 can be provided for interfacing with chipset 960. Such user interface components 985 can include a keyboard, a microphone, touch detection and processing circuitry, a pointing device, such as a mouse, and so on. In general, inputs to system 950 can come from any of a variety of sources, machine generated and/or human generated.

Chipset 960 can also interface with one or more communication interfaces 990 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 955 analyzing data stored in storage 970 or 975. Further, the machine can receive inputs from a user via user interface components 985 and execute appropriate functions, such as browsing functions by interpreting these inputs using processor 955.

It can be appreciated that exemplary systems 900 and 950 can have more than one processor 910 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some configurations the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Claim language reciting "at least one of" a set indicates that one member of the set or multiple members of the set satisfy the claim. Tangible computer-readable storage media, computer-readable storage devices, or computer-readable memory devices, expressly exclude media such as transitory waves, energy, carrier signals, electromagnetic waves, and signals per se.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for characterizing scattering in a medium of a Light Detection And Ranging (LiDAR) system, comprising:
    obtaining off-axis power return characteristics with respect to a first wavelength of light and on-axis power return characteristics for at least the first wavelength of light;
    estimating at least one beam attenuation coefficient (c) based on the off-axis power return characteristics and common volume parameter function for the LiDAR system and an extinction coefficient ($\alpha$) for the medium based on the on-axis power return characteristics; and
    extracting a value for at least one diffuse attenuation coefficient ($K_d$) for the medium using a beam spread parameter for the LiDAR system (D) and a pre-defined relationship between $\alpha$, c, D, and $K_d$.

2. The method of claim 1, wherein the off-axis power return characteristics comprise a total energy multiple scattering (MS) return, a total energy single scattering return, and a beam spread for the first wavelength of light.

3. The method of claim 2, wherein estimating the beam attenuation coefficient comprises computing a ratio of a total power during a Non-Common Volume Scattering (NCV) period and a total power during the a Common Volume Scattering (CV) period scaled by the common volume parameter for the first wavelength of light, wherein the total power during the NCV period is derived from the total energy MS return, and wherein the total power during the CV period is derived from the total energy SS return.

4. The method of claim 1, wherein the on-axis power return characteristics comprise an instantaneous power as a function of time, the peak instantaneous power, and the slope of decay of instantaneous power.

5. The method of claim 1, further comprising:
    adjusting imaging data for the LiDAR system based on value at least one of $K_d$ or c.

6. The method of claim 1, wherein the first wavelength is in the range between 350 nm and 750 nm.

7. The method of claim 1, further comprising obtaining the on-axis power return characteristics for at least one second wavelength of light and performing the estimating and extracting based on the on-axis power characteristics for the first wavelength of light and at least one second wavelength of light.

8. A Light Detection And Ranging (LiDAR) system, comprising:
    a light source;
    an on-axis sensor;
    an off-axis sensor;
    a computing system coupled to at least the on-axis sensor and the off-axis sensor, the computing system comprising a processor and a memory having stored therein instructions for causing the process to perform the steps of:
    obtaining, from the off-axis sensor, off-axis power return characteristics with respect to a first wavelength of light generated by the light source;
    obtaining, from the on-axis sensor, on-axis power return characteristics for at least the first wavelength of light;
    estimating at least one beam attenuation coefficient (c) based on the off-axis power return characteristics and common volume parameter function for the LiDAR system and an extinction coefficient ($\alpha$) for the medium based on the on-axis power return characteristics; and
    extracting a value for at least one diffuse attenuation coefficient ($K_d$) for the medium using a beam spread parameter for the LiDAR system (D) and a pre-defined relationship between $\alpha$, c, D, and $K_d$.

9. The system of claim 8, wherein the off-axis power return characteristics comprise a total energy multiple scattering (MS) return, a total energy single scattering return, and a beam spread for the first wavelength of light.

10. The system of claim 9, wherein estimating the beam attenuation coefficient comprises computing a ratio of a total power during a Non-Common Volume Scattering (NCV) period and a total power during the a Common Volume Scattering (CV) period scaled by the common volume parameter for the first wavelength of light, wherein the total power during the NCV period is derived from the total energy MS return, and wherein the total power during the CV period is derived from the total energy SS return.

11. The system of claim 8, wherein the on-axis power return characteristics comprise an instantaneous power as a function of time, the peak instantaneous power, and the slope of decay of instantaneous power.

12. The system of claim 8, further comprising:
adjusting imaging data for the LiDAR system based on value at least one of $K_d$ or c.

13. The system of claim 8, wherein the first wavelength is in the range between 350 nm and 750 nm.

14. The system of claim 8, further comprising obtaining the on-axis power return characteristics for at least one second wavelength of light generated by the light source and performing the estimating and extracting based on the on-axis power characteristics for the first wavelength of light and at least one second wavelength of light.

15. A computer-readable medium having stored therein a computer program for causing a computing device to characterize scattering in a medium of a Light Detection And Ranging (LiDAR) system, the computer comprising a plurality of code sections for:
obtaining off-axis power return characteristics with respect to a first wavelength of light and on-axis power return characteristics for at least the first wavelength of light;
estimating at least one beam attenuation coefficient (c) based on the off-axis power return characteristics and common volume parameter function for the LiDAR system and an extinction coefficient ($\alpha$) for the medium based on the on-axis power return characteristics; and
extracting a value for at least one diffuse attenuation coefficient ($K_d$) for the medium using a beam spread parameter for the LiDAR system (D) and a pre-defined relationship between $\alpha$, c, D, and $K_d$.

16. The computer-readable medium of claim 15, wherein the off-axis power return characteristics comprise a total energy multiple scattering (MS) return, a total energy single scattering return, and a beam spread for the first wavelength of light.

17. The computer-readable medium of claim 16, wherein estimating the beam attenuation coefficient comprises computing a ratio of a total power during a Non-Common Volume Scattering (NCV) period and a total power during the a Common Volume Scattering (CV) period scaled by the common volume parameter for the first wavelength of light, wherein the total power during the NCV period is derived from the total energy MS return, and wherein the total power during the CV period is derived from the total energy SS return.

18. The computer-readable medium of claim 15, wherein the on-axis power return characteristics comprise an instantaneous power as a function of time, the peak instantaneous power, and the slope of decay of instantaneous power.

19. The computer-readable medium of claim 15, further comprising:
adjusting imaging data for the LiDAR system based on value at least one of $K_d$ or c.

20. The computer-readable medium of claim 15, further comprising obtaining the on-axis power return characteristics for at least one second wavelength of light and performing the estimating and extracting based on the on-axis power characteristics for the first wavelength of light and at least one second wavelength of light.

* * * * *